United States Patent [19]
Glenn et al.

[11] Patent Number: 5,958,589
[45] Date of Patent: Sep. 28, 1999

[54] STARCH-BASED MICROCELLULAR FOAMS

[75] Inventors: Gregory M. Glenn, American Canyon; Donald J. Stern, Berkeley, both of Calif.

[73] Assignee: The United States of America as represented by the Secretary of Agriculture, Washington, D.C.

[21] Appl. No.: 08/857,348

[22] Filed: May 16, 1997

Related U.S. Application Data

[62] Division of application No. 08/499,592, Jul. 7, 1995, abandoned.

[51] Int. Cl.$^6$ ..................................................... B32B 5/16
[52] U.S. Cl. .................. 428/402.2; 516/105; 106/674; 106/122; 428/321.5
[58] Field of Search ................... 428/402.2, 321.5; 252/307, 315.3; 106/674, 122

[56] References Cited

U.S. PATENT DOCUMENTS

| | | | |
|---|---|---|---|
| 3,081,181 | 3/1963 | Rutenberg et al. | 106/122 |
| 3,128,208 | 4/1964 | Zeitlin et al. | 127/71 |
| 3,128,209 | 4/1964 | Peekskill et al. | 127/71 |
| 3,334,052 | 8/1967 | Kurz et al. | 252/315.3 |
| 4,138,356 | 2/1979 | Vincent et al. | 428/402.2 |
| 4,642,903 | 2/1987 | Davies | 34/284 |
| 4,755,377 | 7/1988 | Steer | 252/315.3 |
| 4,863,655 | 9/1989 | Lacourse et al. | 106/122 |
| 4,985,082 | 1/1991 | Whistler | 252/315.3 |
| 5,215,756 | 6/1993 | Gole et al. | 424/484 |
| 5,254,598 | 10/1993 | Schameus et al. | 521/54 |
| 5,360,828 | 11/1994 | Morrison | 106/122 |
| 5,612,385 | 3/1997 | Ceaser et al. | 521/68 |
| 5,705,536 | 1/1998 | Tomka | 521/84.1 |

FOREIGN PATENT DOCUMENTS

| | | | |
|---|---|---|---|
| PCT/US93/ 05993 | 6/1993 | WIPO | C08J 9/30 |

OTHER PUBLICATIONS

Glenn et al., "Starch–Based Microcellular Foams", *Cereal Chem.* vol. 72(2) Mar.–Apr. 1995, pp. 155–161.

Archival printouts of information published on Knight–Ridder File 60 (CRIS/USDA) for Project No. 5325–14000–025–00D in 1992, 1993, 1994, and 1995 and CRIS fax transmittal cover memo dated Oct. 15, 1996.

S.S. Kistler, "Coherent Expanded Aerogels and Jellies," *Nature* 127:741 (1931).

S.S. Kistler, "Coherent Expanded Aerogels," *Journal of Physical Chemistry* 32:52–64 (1932).

J. Fricke, "Aerogels—a Fascinating Class of High–Performance Porous Solids," *Aerogels*, Ed. J. Fricke, Springer–Verlag, New York, pp. 1–19 (1985).

F. R. Senti and S. R. Erlander, "Carbohydrates," Chapter 9 in *Non Storchiometric Compounds*, Ed. M. L. Mandelcorn, Academic Press, New York, pp. 568–605 (1964).

*Food Polysaccharides and Their Applications*, Ed. A. M. Stephen, Marcel Dekker, Inc., pp. 29–30 (1995).

G. A. Reineccius, "Flavor Encapsulation," *Food Reviews International* 5:147–176 (1989).

F. Shahidi and X–Q Han, "Encapsulation of Food Ingredients," *Critical Reviews in Food Science and Nutrition* 33:501–547 (1993).

*Primary Examiner*—Richard D. Lovering
*Assistant Examiner*—Daniel S. Metzmaier
*Attorney, Agent, or Firm*—M. Howard Silverstein; John D. Fado; Margaret A. Connor

[57] ABSTRACT

Starch-based microcellular foams composed of a solid matrix with a network of small open cells or pores are described. The foams have high pore volume, low density, and high surface area, and are prepared using a process wherein an aqueous gel prepared from gelatinized starch is treated to exchange the water in the gel with air while maintaining the integrity of the network of open cells or pores. The starch-based microcellular foams are particularly useful for encapsulation and later release of a substance.

5 Claims, 9 Drawing Sheets

FIG. 9

STARCH-BASED MICROCELLULAR FOAMS

This application is a division of application Ser. No. 08/499,592, filed Jul. 7, 1995, now abandoned.

BACKGROUND OF THE INVENTION

1. Field of the Invention

The present invention relates generally to foams having a solid phase matrix with air-filled pores. More specifically, the present invention relates to starch-based microcellular foams having high pore volume, low density, and high surface area. The invention further relates to methods of preparing the foams from starch aquagels. The starch-based microcellular foams are particularly useful for encapsulation and release of compounds such as flavoring compounds, fragrances, and pharmaceuticals.

2. Description of the Art

Starch is an important agricultural product that, in the United States, is derived primarily from corn, potatoes, and wheat. In its raw state, starch is in the form of dense granules that range in size from 2 microns in wheat starch to over 100 microns in potato starch. Granular starch is utilized in many food and non-food products and is often chemically modified to further expand its uses. Starch may be heated in the presence of water to cause the starch granules to gelatinize. Gelatinization is the swelling and hydration of starch granules which result in the disruption of molecular order within the granule and solubilization of the starch molecules.

Starch granules are generally primarily composed of two polymers: amylose (linear) or amylopectin (branched), with the largest portion being amylopectin (70–85%). However, starch granules from certain plant varieties are almost entirely amylopectin (98%) while others may contain 45% to 80% amylose. Amylose is a polymer of (1-4)-linked α-D-glucopyranosyl units with a molecular weight that varies depending on the source of the starch but is generally much smaller than that of amylopectin. Amylopectin has short branches on only about 4% of the D-glucosyl residues. Amylopectin molecules range from about 50 to 100 million daltons in molecular weight. Aqueous starch solutions that have been heated to initiate gelatinization can be cooled to initiate gelation, the process of gel solidification that occurs as the aqueous starch gels are cooled or aged. Gelation appears to be dominated by the amylose content of starch even though it may not be the major fraction. Gelation takes place as molecular reassociation of the hydrated and dispersed starch molecules occurs, presumably through hydrogen bonding in the aqueous gel.

The gelation properties of starch have been exploited in the food industry to make products with desirable texture. High amylopectin starches have been used to make puddings with soft, creamy textures. Wheat and regular dent corn starches contain 23 to 28% amylose and can be gelatinized and allowed to undergo the gelation process to form firm aqueous gels. High amylose corn starches are also commercially available which form unusually firm aqueous gels at low concentrations.

SUMMARY OF THE INVENTION

The present invention comprises unique starch-based microcellular foams composed of a solid matrix with small air-filled cells or pores. The starch-based foams of the invention are prepared using a novel process wherein a firm aqueous gel (aquagel) prepared from gelatinized starch is treated to exchange the water in the aquagel with air while maintaining the network of open cells or pores in the structure. In brief, this is carried out by equilibrating the aquagel in a first exchange liquid which has a nonaqueous liquid component that is miscible with water and that is effective for displacing water in the aquagel. Next, the first exchange liquid is removed under conditions which maintain the network of open cells or pores in the structure. In one method, the first exchange liquid is equilibrated with a second exchange liquid which is a nonaqueous liquid that is miscible with the first exchange liquid and that is effective for displacing the first exchange liquid. Then, the second exchange liquid is exchanged with air. In another method, the first exchange liquid is displaced with air directly.

The starch-based microcellular foam can be formed into slabs, cylinders, spheres, or other shapes. The properties of the foam products vary depending on the type of starch that is used and the shape of the starch-based microcellular foam product.

The products of the invention have unique and useful properties, including high porosity, low density, and high surface area. They have the advantage of being a food grade material and thus are useful for both food and nonfood applications.

In one aspect of the invention, starch-based foams of the invention are useful to encapsulate a substance for release at a later time. The starch foams lose their microporous structure when placed in contact with water, and thus water can be used to disrupt the foam structure to release the encapsulated substance. Thus, the invention finds particular use as a carrier and release agent for chemicals including flavoring compounds, pharmaceuticals, pheromones, fragrances, pesticides, repellents.

Another aspect of the invention is use of the starch-based microcellular solid foams of the invention as insulation materials.

Still a further aspect of the invention is use of the foams of the invention as oil absorbants, for example to absorb oils such as perfume oil essences, or for cleaning up oil spills, or as absorbants for nonpolar liquids.

A still further aspect of the invention is as a precursor for making a rigid, starch-based plastic for use in non-aqueous environments or for use for biodegradable items.

Other objects and advantages of the present invention will become readily apparent from the ensuing description.

DESCRIPTION OF THE DRAWINGS

FIG. 5 shows a comparison between (Z)-(3)-hexenal admixed with different media at 2% (vol/wt) and head-space sampled over 20 days. The Y axis shows GC integrated peak areas in mV/sec. The X axis lists the series of preparations as follows: The first series of bars, labeled b-C was a preparation of (Z)-3-hexenal and β-cyclodextrin done as above with starch-based microcellular foam. Series St-F was a preparation of starch-based microcellular foam and (Z)-3-hexenal. The third series labled Hyl was a preparation of starch-based microcellular foam, staring material, Hylon VII and (Z)-3-hexenal. Series four, Vap, is a sample of odorant alone. The Z axis is number of days, starting at day 0.

FIGS. 7 and 8 compare encapsulation properties of starch-based microcellular foam and β-cyclodextrin.

DETAILED DESCRIPTION OF THE INVENTION

The present invention provides novel starch-based microcellular foam products composed of a solid matrix having a network of small air-filled cells or pores. The foams have the properties of high pore volume, low density, and high surface area. They are prepared using a novel process wherein a firm aqueous gel (aquagel) prepared from gelatinized starch is treated to exchange the water in the aquagel with air under conditions which minimize the effects of surface tension to thereby maintain the integrity of the network of open cells in the structure.

The starch-based microcellular foam products can be formed into slabs, cylinders, spheres, or other shapes. The properties of the foam products vary depending on the type of starch used and the shape or geometry of the foam product.

Preparation of Starch-Based Microcellular Foams

The starch-based microcellular foams of the invention are prepared by a unique process by wherein a firm aqueous gel (aquagel) prepared from gelatinized starch is dried under conditions that minimize the effects of surface tension on the gel to thereby obtain a dry, porous solid having an open network of cells or pores in the structure (an aerogel). In brief, this is carried out by equilibrating the aquagel in a first exchange liquid that has a nonaqueous liquid component that is miscible with water and that is effective for displacing water in the aquagel. Equilibration is carried out for a time sufficient to displace at least about 80% of the water in the aquagel with the nonaqueous liquid component to obtain an intermediate gel containing the nonaqueous liquid. Next, the first exchange liquid is removed under conditions which maintain the integrity of the open network of cells or pores in the structure. In one method, the first exchange liquid is removed by equilibrating with a second exchange liquid which is a nonaqueous liquid that is miscible with the first exchange liquid and is effective for displacing the first exchange liquid. Then, the second exchange liquid is displaced with air. In another method, the first exchange liquid is displaced with air directly.

The starch-based microcellular foam products of the invention can be prepared using (1) unmodified starch such as obtained from any agricultural starch-producing crop, including wheat, corn, rice, potato, peas, tapioca, and other grains and vegetable starches, and including high amylose starch; (2) modified starch, that is, starch that has been modified by hydrolysis or dextrinization, or has been modified to change the chemical structure of some of the D-glucopyranosyl units in the molecule such as by oxidation, esterification or etherification; (3) mixtures of different unmodified starches; (4) mixtures of different modified starches, and (5) mixtures of unmodified and modified starches. It is preferred that starch starting material contain at least about 20% amylose.

First, an aquagel is prepared from gelatinized starch. Typically, this is carried out as follows. The starch is mixed together with water in an amount that is sufficient to disperse the starch and allow for gelatinization to occur and sufficient to form an aquagel subsequent to gelatinization. Generally, the range of concentration of starch to initial water is about 1% to 20%. The preferred concentration range can vary with the type of starch, and can be readily determined by trial runs. In the case of unmodified wheat starch, the preferred concentration of starch to initial water is about 6–10%, and the most preferred concentration is about 8%. In the case of unmodified high amylose starch, the preferred concentration of starch to initial water is about 5–8%, and the most preferred concentration is about 8%.

The aqueous starch mixture is treated to gelatinize the starch granules, that is, to cause the starch granules to swell and hydrate and cause solubiliztion of the starch molecules, thereby disrupting the molecular order within the granules. Generally, this is accomplished by mixing and heating the starch mixture at or above the gelatinization temperature of the starch for a time sufficient to achieve starch gelatinization. One way to determine galvanization is to observe the loss of the starch birefringence. Another way is to measure viscosity of the heated starch-water mixture. Viscosity will increase to a maximum and decrease, indicating gelatinization has occurred.

Where a particular foam shape is desired, the gelatinized starch is treated to obtain the desired form of the foam product. The gelatinized starch can be cast as a layer or shaped article. For example, where cylindrical, slab or other molded shapes are desired, the aqueous gelatinized starch is poured into a mold having the desired shape. Alternatively, as discussed below, the starch can be poured or injected into a liquid to form starch aquagel spheres.

Next, the gelatinized starch is cooled or aged to cause gelation of the gelatinized starch. Gelation is used herein to describe the process of rigidity development (solidification) wherein the gelatinized starch sets into a firm aqueous gel, denoted as an aquagel. For purposes of this invention, a firm aquagel is defined to mean that the aquagel has sufficient firmness so that a molded aquagel can be removed a mold without undue tearing of the formed aquagel, and that aquagel spheres can be removed from oil and washed without undue destruction of the spheres.

As noted above, spherical-shaped microcellular foam products can be formed without a shaping step by pouring or injecting the gelatinized starch as a hot starch melt through an orifice into oil or other liquid that is immiscible in water or into a gas, to induce the formation of the aquagel spheres. It is preferred that the liquid or gas is chilled to cool the starch spheres and augment the formation of aquagels. The size of the spheres is determined by the temperature of the melt, the injection pressure, and the size of the orifice through which the melt is injected. As the spheres are cooled and settle to the bottom of the container, they form aquagels. The water-immiscible liquid is removed from the spheres using detergent or organic solvent, e.g., hexane, washes.

Next, the aquagel is treated to replace the water in the gel with air, while maintaining an open porous network in the gel structure. The foams of the inventions can not be obtained simply by direct air drying of the starch aquagel. This is because the surface tension created within the cells or pores of the aquagel while air drying causes the starch aquagel to shrink and collapse, and form a hard, dense mass. In order to obtain a starch-based foam having a network of open cells or pores, the starch aquagel must first be equilibrated in a first exchange liquid that has nonaqueous liquid component that is effective for displacing water in the aquagel, that is miscible with water, that can be readily volatilized, that has a lower surface tension than water, and that does not substantially solubilize the starch. The equilibration is carried out for a time sufficient to displace at least about 80% of the water in the aquagel with the nonaqueous liquid, preferably about 90%, and more preferably 95–100%. This equilibration results in the formation of an intermediate gel containing the nonaqueous liquid. As shown in the examples, below, equilibration may be carried out using several equilibration steps and successively increasing concentrations of the nonaqueous liquid. It is preferable that aquagels that are 2.5 cm thick or thicker are equilibrated with at least three concentrations of ethanol, e.g., 40%, 70%, and 100%. In some cases, four concentrations may be preferred, e.g., 40%, 60%, 80%, and 100%. The optimum equilibration parameters for any particular aquagel can readily be determined by trial runs. Exemplary nonaqueous liquids useful for equilibration include ethanol, methanol, and acetone.

Next, the first exchange liquid in the intermediate gel is removed under conditions which maintain the network of open cells or pores in the structure. In one method, the intermediate gel is equilibrated with a second exchange liquid which is a nonaqueous liquid that is effective for displacing the first exchange liquid, that is miscible in the first exchange liquid, that can be readily volatilized, that has a lower surface tension than the first exchange liquid, and that does not substantially solubilize the starch. The equilibration is carried out for a time sufficient to displace at least about 80% of the first exchange liquid with the second exchange liquid, and preferably about 90%, and more preferably 95–100%. Then, the second exchange liquid is displaced with air. This is carried out, for example, by air drying or by critical point drying. Exemplary of the second liquid is liquid carbon dioxide. For example, where $CO_2$ is used, it can be conveniently displaced with air by elevating the temperature and pressure to reach the critical point of the $CO_2$. The pressurized $CO_2$ is then released leaving a dry starch foam having been exposed to minimal surface tension.

In another method, the first exchange liquid is displaced with air directly. This can be carried out, for example, by evaporation of the liquid in air (air drying), by critical point drying, or by drying under reduced pressure. In all cases, displacement of the exchange liquid to obtain an aerogel foam is carried out so as to maintain the integrity of the porous microcellular starch structure.

It is understood that additional exchange liquids may be employed subsequent to the second exchange liquid and prior to displacement with air as desired.

The foregoing methods provide a dry starch-based product having a solid phase matrix interspersed with open air-filled cells or pores. For purposes of this invention, the terms "cells" and "pores" are used interchangeably.

Aquagels from some starches, for example, high amylose starch, may not be strong enough for direct air drying of the intermediate gel. In these cases, the first exchange liquid is exchanged with air by critical point drying or by equilibrating the first exchange liquid in a second exchange liquid as described above.

Properties and Uses of the Starch-Based Foams

The starch-based microcellular foams of the invention have unique physical and mechanical properties. They are characterized by having low density, high pore volume, small pore size, and large surface area. Typically, the density in the foam is about 0.32 gm/cm$^3$ or less; and the ratio of air to solid in the foam is at least about 15% air, and preferably at least 40% air. The surface area is typically at least 50 m$^2$/gm or greater. The size of the cells or pores depends primarily on the starting starch. Generally, at least 80% of the cells or pores are 10 $\mu$m in diameter or less (see FIG. 2).

Starch foams prepared from high amylose starch (at least 40% or greater amylose) are useful for encapsulation of substances such as chemicals, liquids or solids, including flavor compounds, pharmaceuticals, fragrances, pesticides, pheromones, animal repellents. The foams are useful in making carbonless paper, powdered oil mixes, perfumed body powders. Encapsulation is defined to mean that a substance is entrapped, entrained, adsorbed, absorbed, or otherwise incorporated into the starch matrix and/or pores. Because of their small pore size, the porous foams of the invention are able to strongly entrap substances. Because the foams lose their microporous structure when placed in contact with water, the encapsulated substance can be readily released by contacting the foam with an aqueous solution. In sum, the foams have the ability to trap the active material and subsequently release the activity, and thus are superior encapsulating agents. In addition, the encapsulation process does not require a heating step, as in most commonly used encapsulation techniques, which may result in loss of low molecular weight flavorant.

A further advantage is that the foams of the invention can be prepared from food grade starches and thus are useful for food and nonfood applications.

The starch-based microcellular foams of the invention have high compressive strength and low thermal conductivity. Typically, they have a semi-rigid structure. Another use of the starch-based microcellular foams of the invention is as an insulation material. They can be coated with a water impermeable coating or used in a nonaqueous environment.

Another use of the foams of the invention is as oil absorbants. For instance, they are useful in granular form to absorb oil spills on floors or other non-absorbent surfaces. The foams can be used in granular form to bind oils with pleasant odors which would be released under proper conditions such as with a body powder during perspiration, or a pet litter during urination, etc. The starch spheres would also be useful as absorbants of unpleasant odors or liquids. The foams would be a useful absorbant for nonpolar liquids and would inhibit their leakage from liquid flow. This application would be useful in containing hazardous chemicals and liquids.

Another use of the starch-based foams of the invention is as a precursor for making a rigid, starch-based plastic, as discussed in detail, below, in Example 3. The starch plastic could be used in non-aqueous environments such as for food trays that are enclosed in a petroleum-based plastic package. The starch plastics would be useful for single-use items and would be readily biodegradable.

EXAMPLES

The following examples are intended only to further illustrate the invention and are not intended to limit the scope of the invention which is defined by the claims.

Example 1

This example describes the preparation of starch-based microcellular foams.

The starch materials used to prepared the foams included unmodified wheat starch (Midsol 50, Midwest Grain Products, Inc., Atchison, Kans.) and unmodified regular (Melogel) and high amylose (Hylon VII) corn starches (National Starch and Chemical Company, Bridgewater, N.J.). The unmodified wheat and corn starches were composed of approximately 28% amylose and 72% amylopectin. The high amylose corn starch contained approximately 70% amylose and 30% amylopectin.

Preparation of the aquagels and displacement of water in the aquagels with ethanol to form alcogels.

Cylindrical Samples of Unmodified Wheat and Corn Starch. Solutions of 8% starch (w/w) were made using distilled water. Wheat and corn starch solutions (500 ml) were mixed at 75 rpm in a viscoamylograph (Brabender, South Hackensack, N.J.) and heated to approximately 95° C. at a rate of 2° C. $min^{-1}$. The temperature of the starch solution was maintained at 95° C. while mixing continued until the peak viscosity was reached (approximately 350 and 650 Brabender units (BU) for wheat and corn starches, respectively).

The gelatinized starches were poured into cylindrical plastic molds (1.56 cm diameter, 11.4 cm length), covered with aluminum foil, and refrigerated (5° C.) overnight, to form firm aquagels. The aquagels prepared from wheat and corn starch were slightly translucent and "jello-like" when removed from the molds. The water in the aquagels was gradually displaced with ethanol by batch equilibration with a succesion of ethanol baths. Each ethanol bath contained two volumes of liquid for each volume of gel. The equilibration time for each bath was 24 hours for cylindrical samples. The sequence of baths was once in 70% (w/w) ethanol and three times in 100% ethanol for the wheat and corn starch aquagel cylinders that were less than 2.5 cm in thickness. As the water within the aquagel matrix was displaced with ethanol, the gels began to shrink and changed from slightly translucent to opaque and white. The volume of wheat and regular corn starch alcogels ranged from 35 to 40% of the original volume of the mold.

Slab Samples of Unmodified Wheat and Corn Starch. Large (71) batches of unmodified wheat and starch solutions (8% w/w) were prepared in a round bottom flask by rigorously mixing while heating in a boiling water bath. Viscosity readings were taken intermittently with a viscometer (Brooksfield, Model RVT, Stoughton, Mass.) to determine when gelatinization was complete. The starch solutions were mixed and heated (95° C.) until viscosity had peaked and begun to decrease. The starch solutions were poured into slab molds (35 cm×43 cm×1.9 cm) and refrigerated overnight to form firm aquagels. The aquagels were removed from the molds and soaked 48 hours in successive baths of ethanol (40%, 70%, 90% and three changes of 100% ethanol). Additional baths and longer incubation times were used for slabs due to their greater thickness. Wheat and corn aquagels thicker than 2 cm tended to curl and tear if dehydrated too fast.

Cylindrical Samples of High Amylose Corn Starch. High amylose corn starch had a much higher gelatinization temperature than wheat or regular corn starch and could not be gelatinized using the viscoamylogaph. High amylose corn starch solutions (8%, w/w) were heated at 2° C. $min^{-1}$ in a 1000 ml pressure reactor (Paar Instrument Co., Moline, Ill.) equipped with a mixer and controller (Model 4843). The solutions were mixed at 330 rpm and heated to 140° C. The solutions were then cooled to 90° C. using an interal cooling coil. The solutions were poured into cylindrical molds, covered, and refrigerated as described above to form firm aquagels. The high amylose corn aquagels were successively equilibrated for 24 hours in each of four baths containing 100% ethanol to form alcogels. The high-amylose corn starch alcogels ranged from 60 to 72% of the mold volume. Due to low shrinkage during dehydration, the high amylose aquagels could be placed directly in 100% ethanol without a danger of curling or tearing the gel.

Slab Samples of High Amylose Corn Starch. High amylose corn starch solutions (8%, w/w) were gelatinized as described above, poured into slab molds (38 cm×21 cm×1.9 cm), and refrigerated (5° C.) overnight to form a firm aquagel. The aquagels were removed from the molds and soaked successively at least 24 hours in each of four baths of 100% ethanol.

Spherical Samples of Unmodified Wheat Starch and High Amylose Corn Starch. The wheat starch solution (8% w/w) was gelatinized by heating to 100° C. in a pressure reactor, and injected into a 101 container of chilled (10° C.) vegetable cooking oil. The container of cooking oil was rotated at approximately 15 rpm during the injection process. The starch solution was injected at a pressure of 20 psi through a manifold containing four needles (23G1). The starch solution formed into spherical aquagels of approximately 2 mm in diameter.

High amylose corn starch solutions (8% w/w) were heated to 140° C. as described above. The starch solutions were cooled to 75° C. before injecting into chilled oil as described above. The gelatinized starch solution was injected at 10 psi. The resulting spherical gels were approximately 2 mm in diameter.

The vessel of chilled oil which contained the spherical gels made of either wheat or high amylose corn starch was placed in a refrigerator overnight which resulted in firm aquagels. The spherical starch aquagels were removed from the oil by filtering through a funnel and filter paper. The spherical gels were cleansed from any remaining oil by three washes in hexane. The spheres were then placed in distilled water until needed. The spherical aquagels were filtered to remove the free distilled water, and equilibrated with four successive baths of 100% ethanol to form alcogels.

Treatment of the Starch Alcogels to Exchange the Ethanol With Air. Various methods were used to replace the ethanol in the alcogel with air to obtain starch-based microcellular foam products of the invention. These included critical point drying, liquid $CO_2$ extraction, and air drying of cylindrical, slab and spherical starch aquagels that had been equilibrated in ethanol.

Critical Point Drying (CPD) of Alcogels. Slabs, spheres, and cylinders equilibrated in 100% ethanol were placed in an autoclave designed to withstand pressures in excess of 12 MPa. The autoclave was first filled with 100% ethanol and then loaded with the starch samples. The autoclave was quickly drained of ethanol and filled with liquid $CO_2$. Several changes (approximately 3/day) of $CO_2$ were made each day to displace ethanol that diffused out of the sample. The $CO_2$ extraction was completed over a 5 day period after which the autoclave was drained to approximately half-full so that the liquid $CO_2$ level just covered the samples. The autoclave was then heated and further pressurized above the critical temperature (30.92° C.) and pressure (7.375 MPa) of $CO_2$. After reaching the critical point of $CO_2$, the chamber was slowly depressurized and the starch-based microcellular foam samples were removed.

Liquid $CO_2$ Extraction of Alcogels. Alcogels were placed in an autoclave and equilibrated with liquid $CO_2$ as described for the CPD process. After the fifth day of $CO_2$ equilibration, the autoclave was slowly depressurized without reaching the critical temperature and pressure of $CO_2$. The starch-based microcellular foam samples were removed.

Air-dying of Alcogels. Alcogels prepared from cylindrical, slab or spheres aquagels were air-dried by placing the samples equilibrated in 100% ethanol on perforated trays covered with sheets of Whatman filter paper. The trays were enclosed in a polyethylene chamber that was continuously flushed with a stream of air that had been dried by filtering through anhydrous $CaSO_4$. The samples were kept in the chamber for one day beyond the time that ethanol odor could be detected in either the effluent or the sample (approximately 4 days), then the starch-based microcellular foam samples were removed.

Properties of the Starch-based Microcellular Foams. The properties of the starch-based microcellular foams of the invention were examined using physical and mechanical tests, Scanning Electron Microscopy (SEM), and light microscopy.

Physical and Mechanical Tests.

Thermal conductivity was measured at a mean temperature of 22.7° C. on three sets of slab samples for each treatment according to standard methods (ASTM C 177-85) using a Thermal Conductivity Instrument (Model GP-500, Sparrell Engineering, Damarascotta, Me.). Readings were taken at one hour intervals as the instrument approached thermal equilibrium. The mean value of at least three measurements was recorded at thermal equilibrium.

The cylindrical samples were used to measure the mechanical properties of the foam. Because, the cylindrical samples of wheat and corn starch tended to shrink while equilibrating in ethanol and often developed a curvature in their length, the dried cylindrical foams were machined into cylinders on a lathe with the final length approximately twice the diameter. The cylinders were conditioned at least 48 hours in an incubator held at 23° C. and 50% relative humidity (ASTM D 1621-73). The samples were tested in compression using a Universal Testing Machine (Model 4500, Instron Corp., Canton, Mass.). Compressive strength was measured at 10% deformation according to ASTM methods (D 1621-73, E6-89). The modulus of elasticity (E) was measured as the ratio of stress to the corresponding strain below the proportional limit of the force-deformation curve. Mechanical tests were performed on four samples for each of four replicates made per treatment.

Density was determined from measurements of sample weight and volume. Moisture content was determined for samples equilibrated at 50% relative humidity or more than two days following AACC method 44-15A (AACC 1983). Total surface area, pore diameters, and pore volume were determined by BET analysis (Porous Materials, Inc., Analytical Services Division, Ithaca, N.Y. 14850).

Results. Starch alcogels that were dried using the $CO_2$ extraction or the CPD processes were similar in density and appearance. Starch alcogels dried by these processes were subjected to very low surface tension forces (Table I) and had final volumes similar to that of their alcogels. The matrix of the high amylose corn starch alcogels did not collapse when dried by either of these two processes. The high amylose corn starch foams were white and opaque and had a final dry density that was much lower than that of wheat and corn starch foams and were only slightly higher than the lowest theoretical density (Table I).

Alcogels dried in air (ethanol in contact with air, Table I) were subjected to much smaller surface tension forces compared to air-dried aquagels (water in contact with air, Table I). (The air-dried aquagels are not in accordance with the invention but were prepared for comparison purposes.) The air dried wheat and corn starch alcogels did not collapse into a thin film during the drying process as did the air-dried aquagels. The air-dried wheat and corn starch alcogels had a mean dry density comparable to samples dried by liquid $CO_2$ extraction and CPD (Table I). The high amylose corn starch alcogels could not be air-dried without collapsing into a dense, translucent mass (Table I).

Samples conditioned at 50% relative humidity had a mean moisture content of 11.5% which largely accounted for the higher density of conditioned foams (compare Table I, II, and III). However, the density of conditioned samples may also have been affected by dimensional changes as the samples aged. The thermal conductivity for air-dried alcogels was higher than for samples prepared by $CO_2$ extraction or CPD (Tables II–IV). There was no significant difference in thermal conductivity for samples prepared by $CO_2$ extraction or CPD. Freeze-dried wheat (Table II) and corn (Table III) starch aquagel samples were prepared for comparison purposes. It should be noted that freeze drying is not in accordance with the invention. These samples had among the highest thermal conductivities recorded for any of the drying techniques even though they had the lowest conditioned densities and thus are not as good an insulating material as the starch foams of the invention. The high amylose corn starch-based microcellular foams (Table IV) had a much lower thermal conductivity than any of the samples tested. The starch-based microcellular foams were compared to an expanded-bead polystyrene foam sample (Table IV). The polystyrene sample had a thermal conductivity similar to those of the CPD wheat (Table II) and corn (Table III) starch foams even though its density was much lower.

Figure 1:
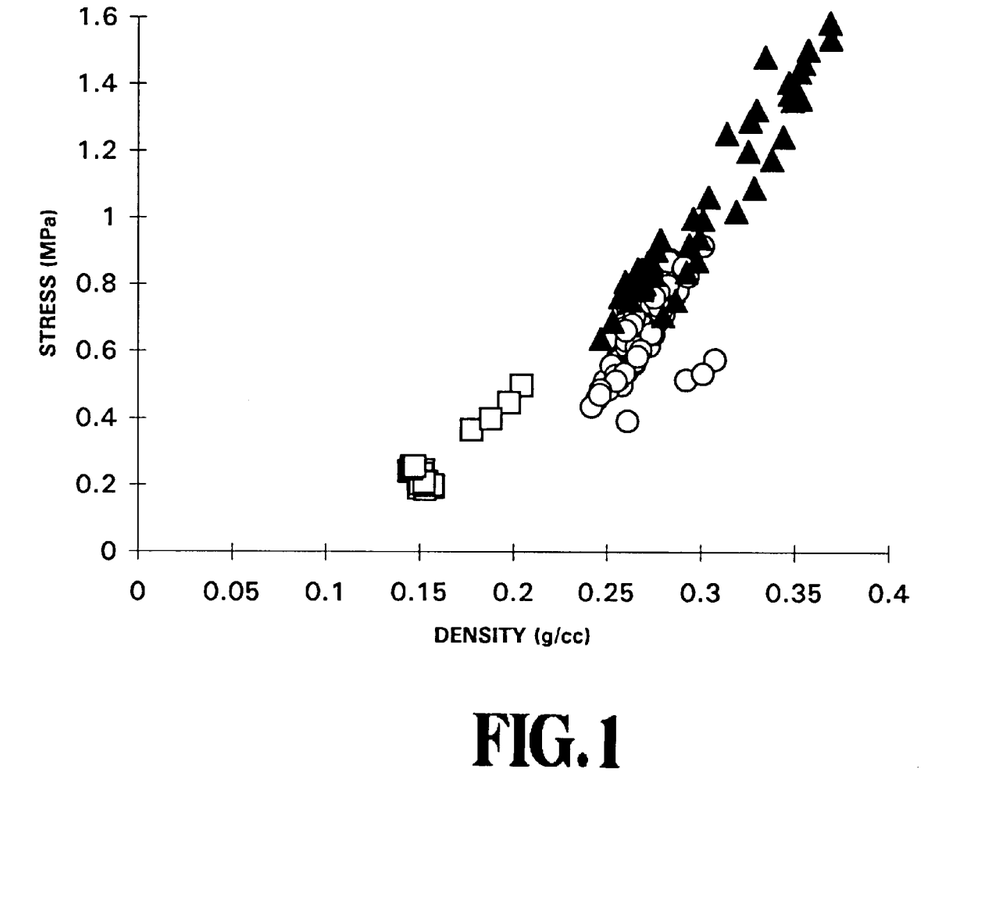
FIG. 1 is a scatter plot of compressive stress and density of starch-based microcellular foams of the invention prepared from wheat starch (▲), corn starch (○), and high amylose corn starch (□). A positive, nearly linear relationship was observed between density and stress.

The mechanical properties of the starch foams appears closely related to density. The relationship between density and compressive strength was positive was nearly linear for starch foams consisting of a wide range in density (FIG. 1). A similar relationship was observed between modulus of elasticity and density. This relationship shows that foams with different densities and mechanical properties can be made.

The mean compressive strengths and densities for wheat and corn starch samples were higher for air-dried samples compared to $CO_2$ extracted and CPD samples although the differences were not statistically significant (P>0.05) due to sample variability (Tables II and III). The corn starch foams had greater compressive strength and density than the wheat starch and high amylose corn starch samples. All the starch foams had much higher compressive strengths and moduli of elasticity than expanded-bead polystyrene (Table II–IV).

The ratio of elastic:plastic deformation resulting from a 10% compressive strain was lowest for the $CO_2$ equilibrated wheat and corn starch foams and highest for the freeze-dried starch foams (foams not in accordance with the invention, but for comparison purposes) (see Tables II and III). The tensile stress required to break wheat and corn starch foams was much less than the compressive stress required to deform the samples ten percent (compare tensile and compressive strength, Tables II and III). The high amylose corn starch foams had tensile and compressive strengths that were similar. In contrast, the expanded-bead polystyrene and freeze-dried starch samples had greater tensile strength than compressive strength (Tables II–IV).

The total surface areas of the starch foams from unmodified corn and high amylose corn were 50 and 145 $m^2/gm$, respectively (Table V). The surface areas for unmodified corn and wheat starch foams was surprisingly dissimlar (Table V) in view of the fact that both have similar amylose:amylopectin ratios. The average pore diameters were similar for foams made from all three starches although the pore size range was greatest for the unmodified corn starch foam Table V). The unmodified corn starch had a much lower total pore volume than the wheat or high amylose corn starch foams. The high amylose corn starch foams had the highest total pore volume (Table V).

TABLE I

Dehydrated Density of Starch Foams Dried Under Varying Conditions

| Substance | Environment | Surface Tension (mN/m) | Theoretical[a] | Density, g/cm3 WS[b] | CS[c] | HACS[d] |
|---|---|---|---|---|---|---|
| Water[h] | Air (18° C.) | 73.05[e] | 0.08 | — | — | — |
| Ethanol | Air (0° C.) | 24.05 | 0.08 | 0.24 (0.008)[f] | 0.25 (0.02) | 1.31 (0.010) |
| $CO_2$ | $CO_2$ Vapor (20° C.) | 1.16 | 0.08 | 0.23 (0.01) | 0.24 (0.004) | 0.11 (0.002) |
| CPD-$CO_2$[g] | | 0.0 | 0.08 | 0.23 (0.008) | 0.24 (0.02) | 0.10 (0.002) |
| Frozen water | Air (freeze dry) | 0.0 | 0.08 | 0.11 (0.003) | 0.10 (0.002) | — |

[a]Lowest density that can be achieved from a gel based on the original gel volume and solids content.
[b]Density of foam sample made from unmodified wheat starch.
[c]Density of foam sample made from unmodified corn starch.
[d]Density of foam sample made from high-amylose corn starch.
[e]Surface tension data from Handbook of Physics and Chemistry (Lide 1992).
[f]Values in parentheses are standard deviations.
[g]Critical point drying.
[h]Not in accordance with the invention. For comparison purposes only.

TABLE II

Physical and Mechanical Properties of Wheat Starch[a]

| Sample | D (g/cm³)[b] | $S_c$ (MPa)[c] | E (MPa)[d] | (W/m · K)[e] | $D_E$ (%)[f] | $D_P$ (%)[g] | $S_u$ (MPa)[h] |
|---|---|---|---|---|---|---|---|
| Air-dried wheat | 0.27[ai] | 0.71[a] | 23[a] | 0.044[a] | — | — | — |
| $CO_2$-extracted | 0.26[a] | 0.57[a] | 21[a] | 0.037[c] | 13[a] | 87[a] | 0.17[a] |
| CPD[j] | 0.26[a] | 0.56[a] | 21[a] | 0.036[c] | — | — | — |
| Freeze-dried[k] | 0.12[b] | 0.23[b] | 2.9[b] | 0.040[b] | 39[b] | 61[b] | 0.46[b] |

[a]Conditioned at least 48 hr at 50% rh.
[b]Density; moisture content of samples was 11.5%.
[c]Compressive strength measured at 10% deformation.
[d]Compressive modulus of elasticity.
[e]Thermal conductivity at 22.7° C. mean temperature. Thermal conductivity of still air is 0.0226 W/m · K.
[f]Elastic deformation expressed as a percentage of the total deformation which equaled 10%.
[g]Plastic deformation expressed as a percentage of the total deformation which equaled 10%.
[h]Tensile strength measured at breaking point.
[i]Values within columns followed by a different letter are significantly different at the 95% confidence level (Fisher's protected least significant difference).
[j]Critical point drying.
[k]Not in accordance with the invention. For comparison purposes only.

TABLE III

Physical and Mechanical Properties of Corn Starch[a]

| Sample | D (g/cm$^3$)[b] | S$_c$ (MPa)[c] | E (MPa)[d] | (W/m · K)[e] | D$_E$ (%)[f] | D$_P$ (%)[g] | S$_u$ (MPa)[h] |
|---|---|---|---|---|---|---|---|
| Air-dried | 0.31[a][i] | 1.14[a] | 36[a] | 0.037[a] | — | — | — |
| CO$_2$-extracted | 0.29[a] | 1.00[a] | 32[a] | 0.033[c] | 13[a] | 87[a] | 0.28[a] |
| CPD[j] | 0.29[a] | 0.97[a] | 33[a] | 0.033[c] | — | — | — |
| Freeze-dried[k] | 0.12[b] | 0.19[b] | 2.9[b] | 0.040[b] | 36[b] | 64[b] | 0.48[b] |

[a]Conditioned at least 48 hr at 50% rh.
[b]Density; moisture content of samples was 11.5%.
[c]Compressive strength measured at 10% deformation.
[d]Compressive modulus of elasticity.
[e]Thermal conductivity at 22.8° C. mean temperature. Thermal conductivity of still air is 0.0226 W/m · K.
[f]Elastic deformation expressed as a percentage of the total deformation which equaled 10%.
[g]Plastic deformation expressed as a percentage of the total deformation which equaled 10%.
[h]Tensile strength measured at breaking point.
[i]Values within columns followed by a different letter are significantly different at the 95% confidence level (Fisher's protected least significant difference).
[j]Critical point drying.
[k]Not in accordance with the invention. For comparison purposes only.

TABLE IV

Physical and Mechanical Properties of High-Amylose Corn Starch and Expanded-Bead Polystyrene (PS)[a]

| Sample | D (g/cm$^3$)[b] | S$_c$ (MPa)[c] | E (MPa)[d] | (W/m · K)[e] | D$_E$ (%)[f] | D$_P$ (%)[g] | S$_u$ (Mpa)[gh] |
|---|---|---|---|---|---|---|---|
| Air-dried | 1.31[a][i] | — | — | — | — | — | — |
| CO$_2$-extracted | 0.16[c] | 0.27[a] | 8.1[a] | 0.024[a] | 27[a] | 73[a] | 0.23[a] |
| CPD[j] | 0.15[c] | 0.22[a] | 5.1[a] | 0.024[a] | — | — | — |
| Beaded polystyrene[k] | 0.019[b] | 0.098[b] | 3.6[b] | 0.036[b] | 25[a] | 75[a] | 0.19[a] |

[a]Conditioned at least 48 hr at 50% rh.
[b]Density moisture content of samples was 11.5%.
[c]Compressive strength measured at 10% deformation.
[d]Compressive modulus of elasticity.
[e]Thermal conductivity at 22.8° C. mean temperature. Thermal conductivity of still air is 0.0226 W/m · K.
[f]Elastic deformation expressed as a percentage of the total deformation which equaled 10%.
[g]Plastic deformation expressed as a percentage of the total deformation which equaled 10%.
[h]Tensile strength measured at breaking point.
[i]Values within columns followed by a different letter are significantly different at the 95% confidence level (Fisher's protected least significant difference).
[j]Critical point drying.
[k]Not in accordance with the invention. For comparison purposes only.

TABLE V

| Sample | Total Surface Area (m$^2$/gm) | Pore Diameter (nm) Average | Pore Diameter (nm) Range | Total Pore Volume (cm$^3$/g) |
|---|---|---|---|---|
| Wheat starch | 116 | 16.5 | 1.5–73 | 0.48 |
| Corn starch | 50 | 13.5 | 1.4–195 | 0.17 |
| High Amylose Corn Starch | 145 | 17.2 | 1.5–97 | 0.63 |

FIG. 2 shows scanning electron micrographs of starch-based microcellular solid foams of the invention compared to other solid cellular materials not in accordance with the invention. Scanning electron micrographs of products of the invention included wheat starch foams (FIGS. 2g,k), regular corn starch foams (FIGS. 2h,l), and high amylose corn starch foams (FIGS. 2i,m). The comparison samples were expanded bead polystyrene (FIGS. 2a,d), puffed wheat (FIGS. 2b,e), wheat starch aquagel that was freeze-dried (FIGS. 2c,f), and transparent silica aerogel (FIGS. 2j,n). Expanded-bead polystyrene (FIGS. 2a,d) and puffed wheat (FIGS. 2b,e) both exhibited a polygonal cell type of microstructure with thin walls. The freeze-dried sample (FIGS. 2c,f) of wheat starch, which was also representative of freeze-dried corn starch foams, consisted of large, thin-walled cells. Very large, nonuniform air-spaces (not shown) were apparent where large ice crystals had grown. The expanded-bead polystyrene foam had the most uniform cell size of the three samples.

Figure 2A:
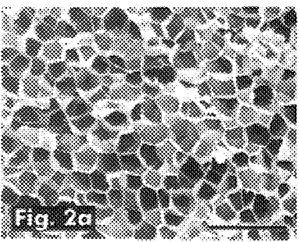
FIG. 2 shows scanning electron micrographs of starch-based microcellular solid foams of the invention compared to other solid cellular materials not in accordance with the invention. Scanning electron micrographs of products of the invention are: wheat starch foams (g,k), regular corn starch foams (h,l), and high amylose corn starch foams (i,m). The comparison samples are: beaded polystyrene (a,d), puffed wheat (b,e), wheat starch aquagel that was freeze-dried (c,f), and transparent silica aerogel (j,n). Magnification bars are as follows: a-c=500 μm; d-f=100 μm; g-j=100 μm; k-n=10 μm. The wheat starch, corn starch, and high amylose corn starch foam products of the invention had much smaller pore sizes than the beaded polystyrene, puffed wheat or freeze-dried wheat starch product. As can be seen in d-f, the beaded polystyrene, puffed wheat, and freeze-dried wheat starch product all contained large cells with sheet-like cell walls. It should be noted that the cells of the beaded polystyrene appear to be of different sizes because the cells are not cut along the same axis. The pore size of the silica aerogel was much too small to discern even at high magnification (n).
Figure 2B:
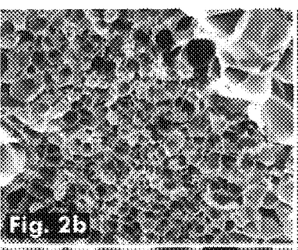
Figure 2C:
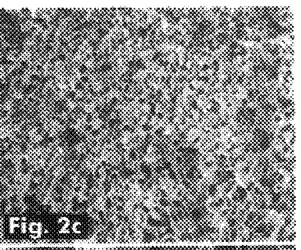
Figure 2D:
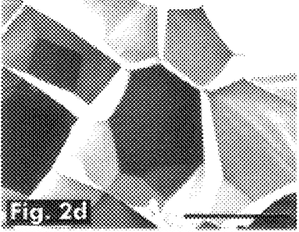
Figure 2E:
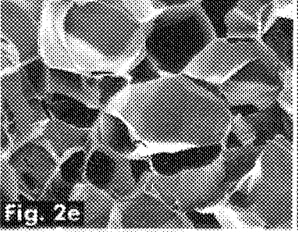
Figure 2F:
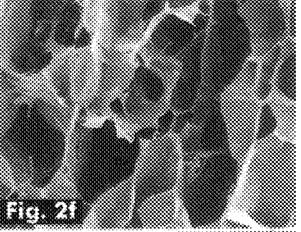
Figure 2G:
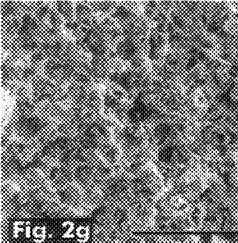
Figure 2H:
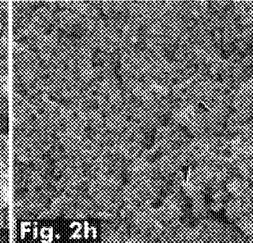
Figure 2I:
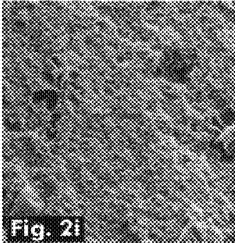
Figure 2J:
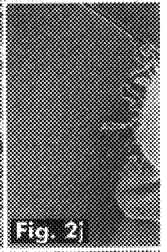
Figure 2K:
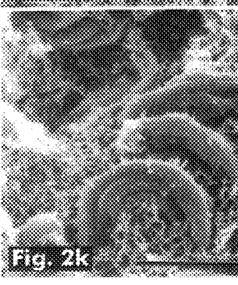
Figure 2L:
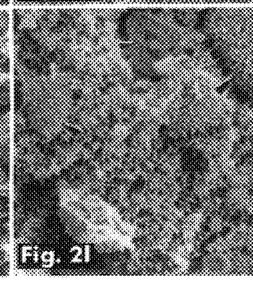
Figure 2M:
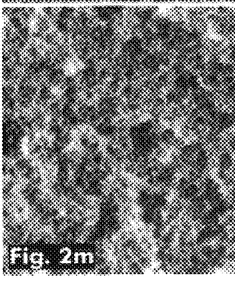
Figure 2N:
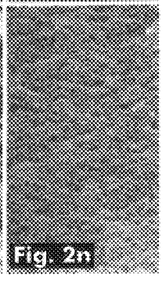

The matrix of the CPD starch-based foams had much smaller pores (<0.25 μm) than the expanded bead polystyrene, puffed wheat and freeze-dried starch foams (FIGS. 2g–m). The porous nature of the starch foams observed at high magnifications (FIGS. 2k–m) revealed a network of small interconnecting strands within the foam matrix. The starch granule remnants interspersed throughout the matrix of the wheat starch foams intern the regular network of strands (FIGS. 2k). The network of strands in the corn starch samples was also interrupted by starch granule remnants but to a lesser degree than in the wheat starch samples. The fine porous nature of the high amylose corn starch samples was less frequently disturbed by the presence of starch granule remnants (FIGS. 2i,m). The upper range in pore sizes of the three starch foams was estimated to be 2 μm. The lower range in pore size was too small to determine from the scanning electron micrographs. However, the fact that high amylose corn starch alcogels cannot be air-dried without collapsing, whereas, the other alcogels can is indirect evidence that high amylose corn starch foams must have a larger percentage of extremely fine pores. Although the silica aerogel appeared as a relatively smooth, solid object (FIGS. 2j,n), it was less dense and more porous than the starch foams but consisted of a microstructure that was also too fine to study using the scanning electron microscope.

Example 2

This example describes encapsulation using the starch-based microcellular foams of the invention.

Materials. Starch-based microcellular foam spheres were prepared from high amylose starch (Hylon VII) as follows. High amylose corn starch solutions (8%, w/w) were heated at 2° C.•min$^{-1}$ in a 1000 ml pressure reactor (Paar Instrument Co., Moline, Ill.) equipped with a mixer and controller (Model 4843). The solutions were mixed at 330 rpm and heated to 140° C. The solutions were then cooled to 75° C. using an interal cooling coil and injected into a 10l container of chilled (10° C.) vegetable cooking oil. The container of cooking oil was rotated at approximately 15 rpm during the injection process. The starch solution was injected at a pressure range of 10 to 20 psi through a manifold containing four needles (23G1). The starch solution formed into spherical aquagels of 1–3 mm in diameter. The vessel of chilled oil which contained the spherical starch gels was placed in a refrigerator overnight. The spherical starch aquagels were removed from the oil by filtering through a funnel and filter paper. The spherical gels were cleansed from any remaining oil by three washes in hexane. The spheres were then stored in distilled water while awaiting the ethanol dehydration step.

The spherical gels were drained of the free water and placed in four successive baths of 100% ethanol. The gels were allowed to equilibrate for at least six hours in each bath to form spherical alcogels. The alcogels were then placed in an autoclave containing 100% ethanol. The autoclave was quickly drained of the free ethanol and filled with liquid $CO_2$. Three changes of liquid $CO_2$ were made each day to displace ethanol that used out of the sample. The $CO_2$ extraction was completed over a 5 day period after which the autoclave was slowly depressurized without reaching the critical temperature and pressure of $CO_2$. The dry starch spheres were removed from the autoclave and placed in a glass container until further use.

The density, pore volume, and pore sizes are shown in Table V. The foam product is hygroscopic and readily loses its microporous structure when placed in contact with water. Because of its extremely small pore size, the starch-based microcellular foam is able to strongly absorb various chemical compounds which can be immediately released when the starch-based microcellular foam is hydrated.

"Hylon" refers to the high amylose corn starch used as the starting material for the starch-based microcellular foam spheres.

(Z)-3-hexenal, 50% solution, was obtained from Bedoukian Corp. This material also contained other isomers, as noted below.

Treatment of encapsulating agent was as follows: (Z)-3-hexenal was dissolved in a few ml of pentane (HPLC grade), slurried with 0.5 grams of encapsulator and allowed to stand for several minutes, followed by evaporation of solvent on a rotary evaporator until encapsulators were observed to be dry and swirled freely. Release of odorant from starch-based microcellular foam spheres was by hydrating with a few ml of water.

β-Cyclodextrin (American Maize Products) is a product which has demonstrated excellent properties of encapsulation by sequestration of odorant.

All gas chromatographic analyses were 1 ml head space samples, analyzed on a HP 5840 gas chromatograph, with flame ionization detector (FID), and a DB-1 column 60 meters×0.32 mm id, at 10 psi Helium.

All conditions of storage and treatment were ambient.

Results.

Figure 6:
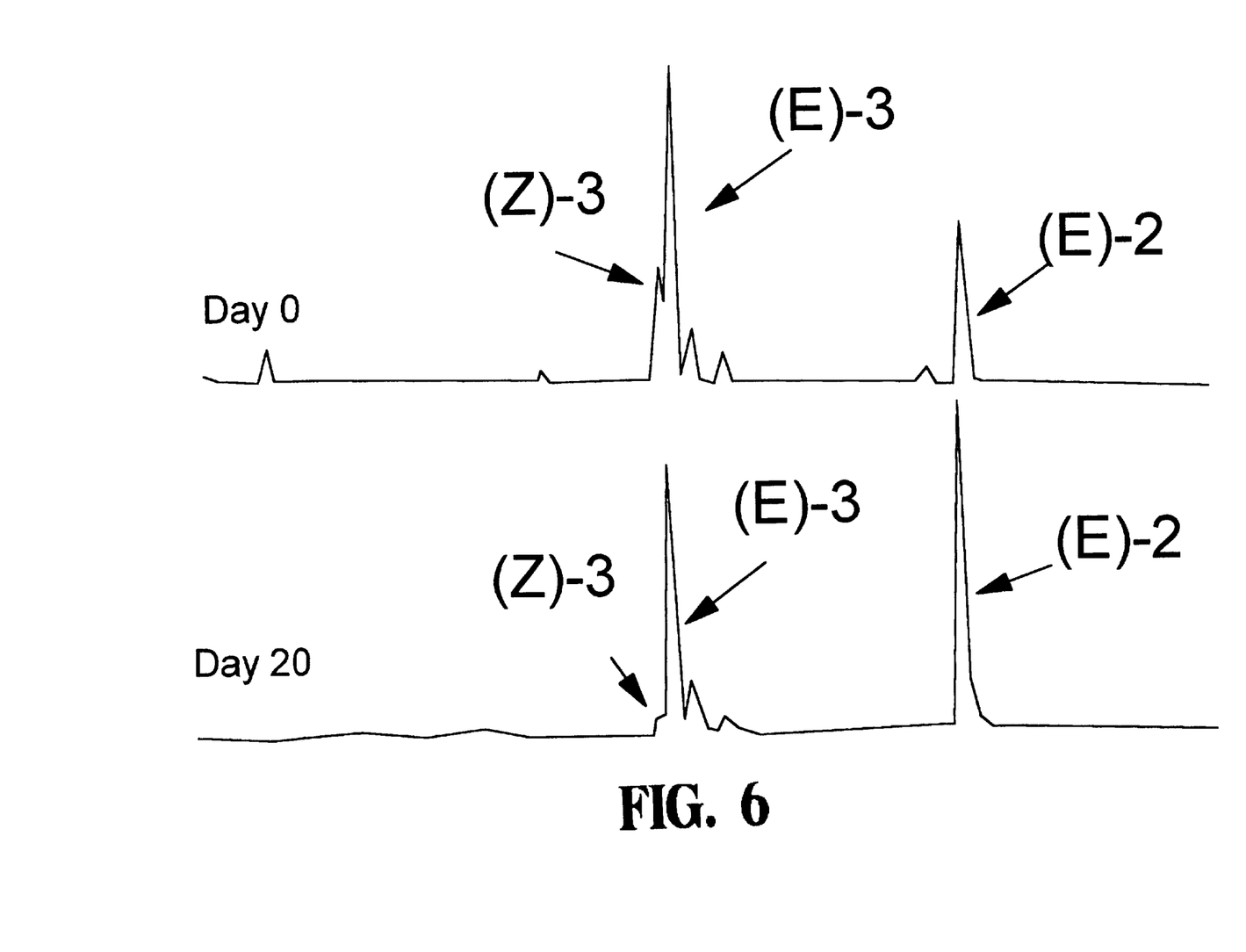
FIG. 6 shows chromatograms of samples of 2% v/w (Z)-3-hexenal on starch-based microcellular foam. The upper graph shows the composition of vapor sample initially, day 0; the lower graph shows composition after 20 days storage.

Encapsulation and Release Properties. The odorant chosen to illustrate the encapsulation and release properties of starch-based microcellular foam was (Z)-3-hexenal because of its instability; it isomizes to (E)-2-hexenal under ambient temperatures, as illustrated by FIG. 6, day 0. The original sample was impure, even when stored at −20 deg F. and it actually contained (E)-3 and (E)-2 hexenals. The initial areas (Mv-sec) of each isomer are noted in FIG. 6 and Table VI. All comparisons of starch-based microcellular foam with other encapsulators, using this system are shown below.

TABLE VI

|  | (Z)-3-hexenal | (E)-3-hexenal | (E)-2-hexenal |
| --- | --- | --- | --- |
| Day 0 | 3994 | 10620 | 5213 |
| Day 20 | 618 | 9011 | 11328 |

Figure 3:
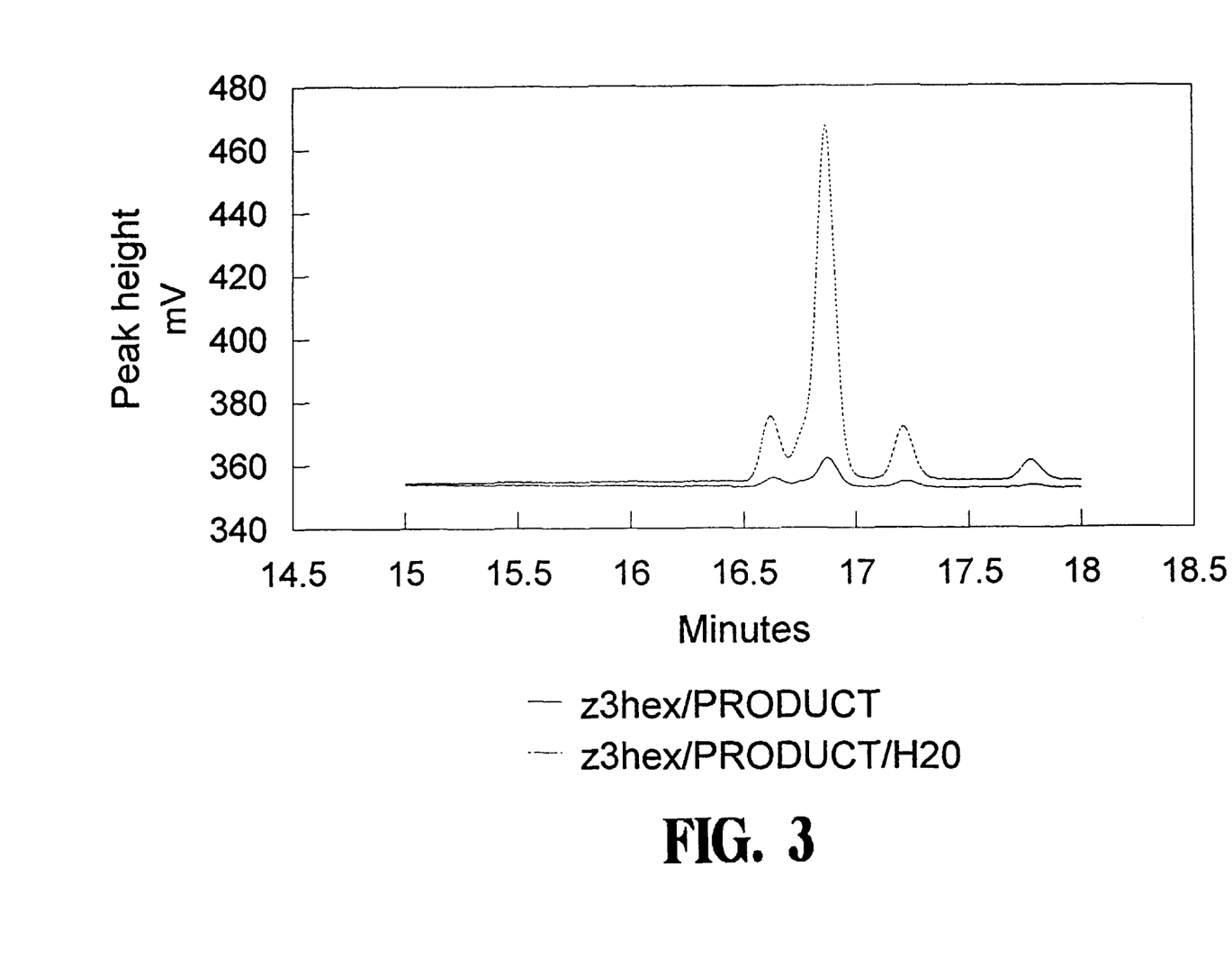
FIG. 3. The upper chromatogram shows the head space analysis of (Z)-3-hexenal/starch-based microcellular foam after hydration. The lower chromatogram shows the head space analysis of hexenal/starch-based microcellular foam before hydration. Y axis=Gas Chromatographic peak height in mV; X axis=Minutes
Figure 4:
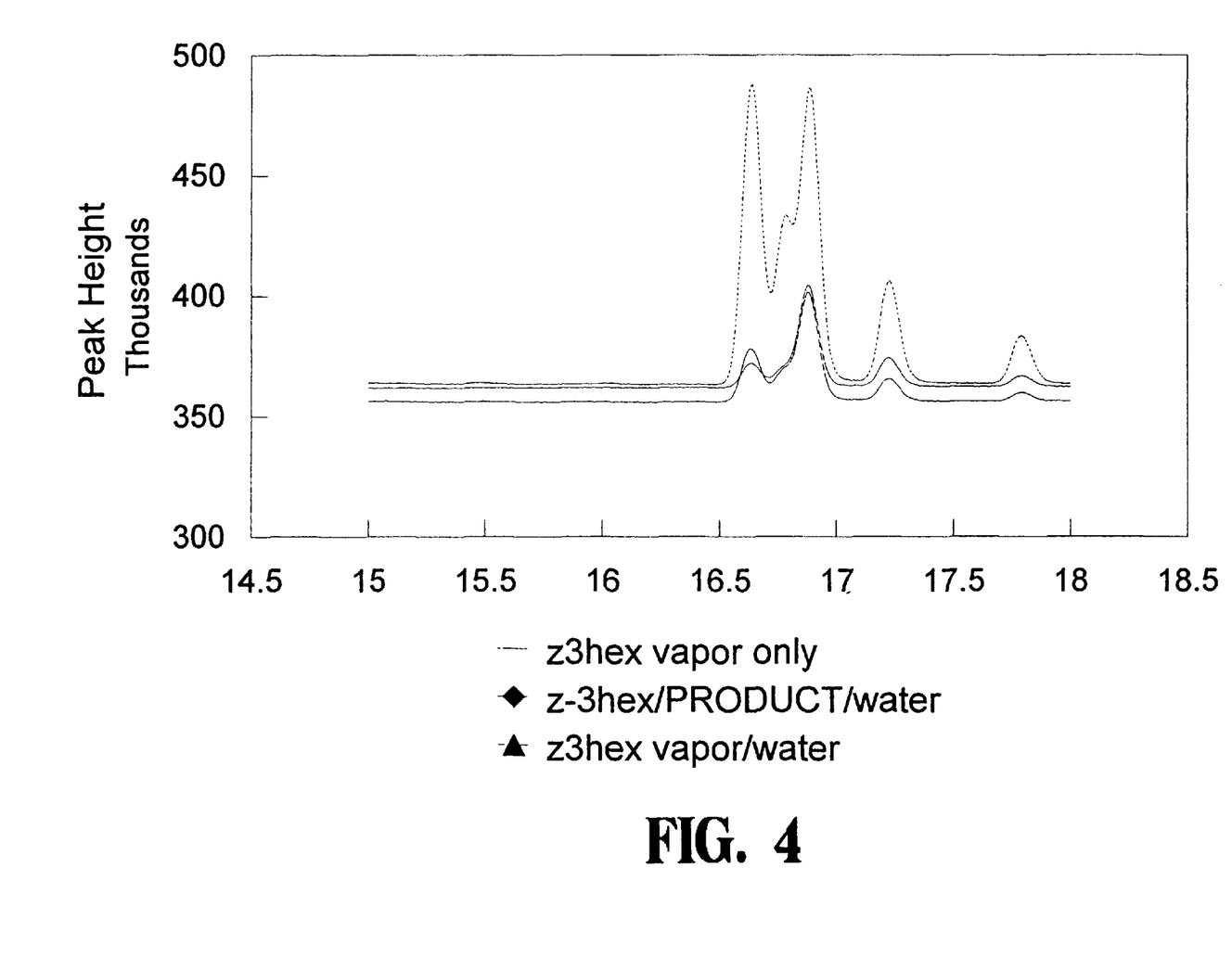
FIG. 4 shows similar chromatograms to FIG. 3 and includes a chromatogram of a mixture of (Z)-3-hexenal and water only, the lowest chromatogram on scale. The X and Y axes same as FIG. 3.

FIGS. 3 and 4 are gas chromatograms which demonstrate the encapsulating properties of starch-based microcellular foam using 2% (vol/wt) of (Z)-3-hexenal. FIG. 3, lower chromatogram represents a vapor sample of hexenal-starch-based microcellular foam complex, the upper chromatograph is a vapor sample of the same complex after the starch-based microcellular foam matrix has been disrupted with the addition of water. There is a significantly greater amount of (Z)-3-hexenal released into the headspace after dissolution of the matrix.

The lower two chromatograms in FIG. 4 show that the hexenal sample eluted from starch-based microcellular foam exerts the same vapor pressure as an equivalent sample of (Z)-3-hexenal mixed with water only. The top most chromatogram shows a pure dry, equivalent, vapor sample of (Z)-3-hexenal. Since water decreases the vapor pressure of hexenal, via a solvent effect, these chromatograms show that there is complete release of hexenal from the starch-based microcellular foam/complex.

Figure 5:
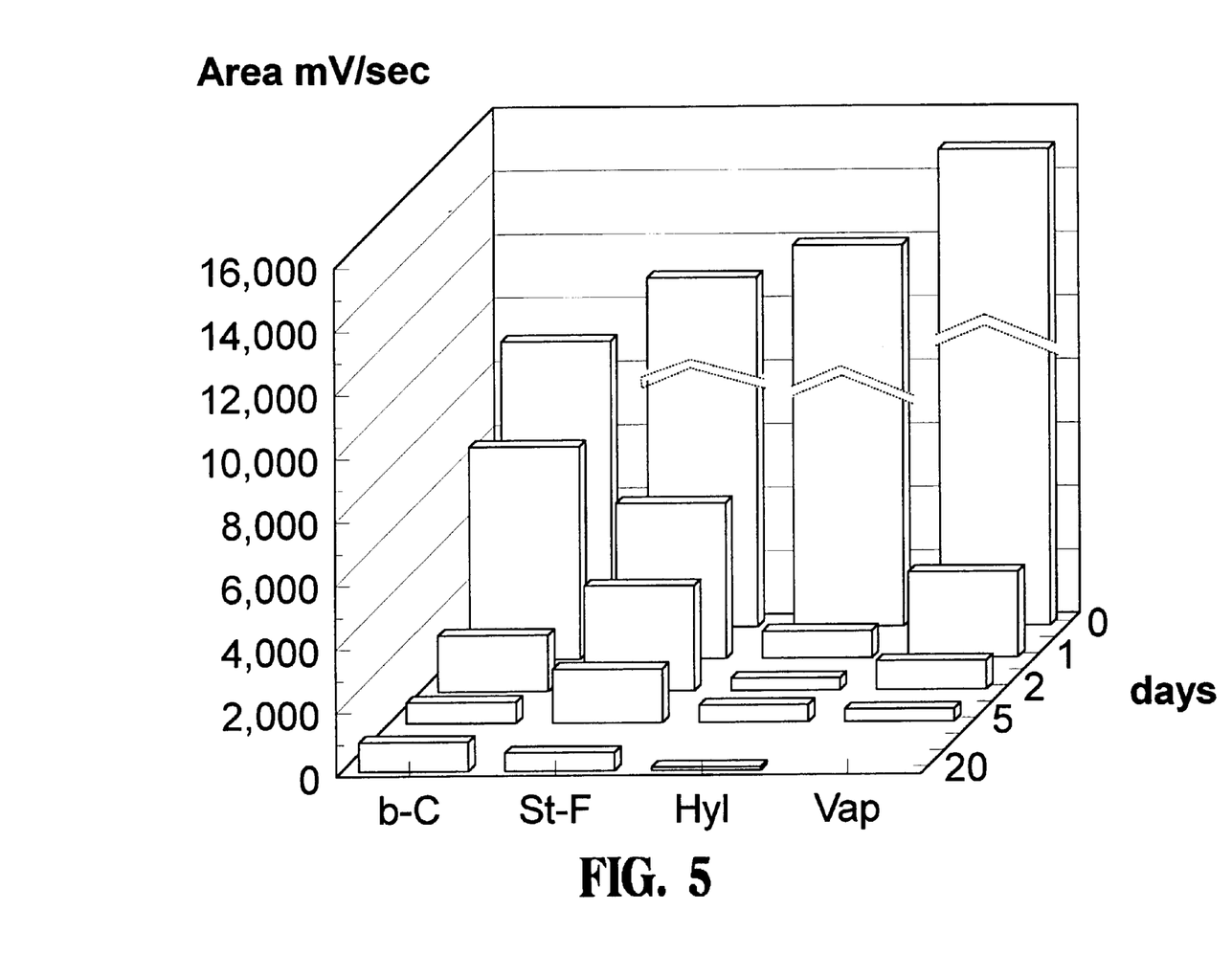

Comparison With Other Encapsulators. Encapsulation properties of 2% (Z)-3-hexenal (v/w) starch-based microcellular foam compared to identical complexes using Hylon VII starting material, β-cyclodextrin and a vapor sample of (Z)-3-hexenal alone, are illustrated in FIG. 5. The values for day 0 were edited in order to more clearly scale the graph and are noted in Table VII.

TABLE VII

| Values for day 0, FIG. 5 | |
| --- | --- |
| β-cyclodextrin | 9700 |
| Starch-based microcellular foam | 14600 |
| Hylon VII | 25200 |
| Vapor only | 165000 |

All samples were stored for 20 days and sampled periodically. The vapor only sample decomposed and could not be detected chromatographically after 20 days. The Hylon VII sample also showed a reduction to an area of 113.

β-cyclodextrin showed a greater conservation of the sample than starch-foam (areas of 919 to 513) but the starch-foam was not optimized vol/wt. (Later illustrations show an optimum for starch-foam to be less than 1% wt/vol.)

Figure 7:
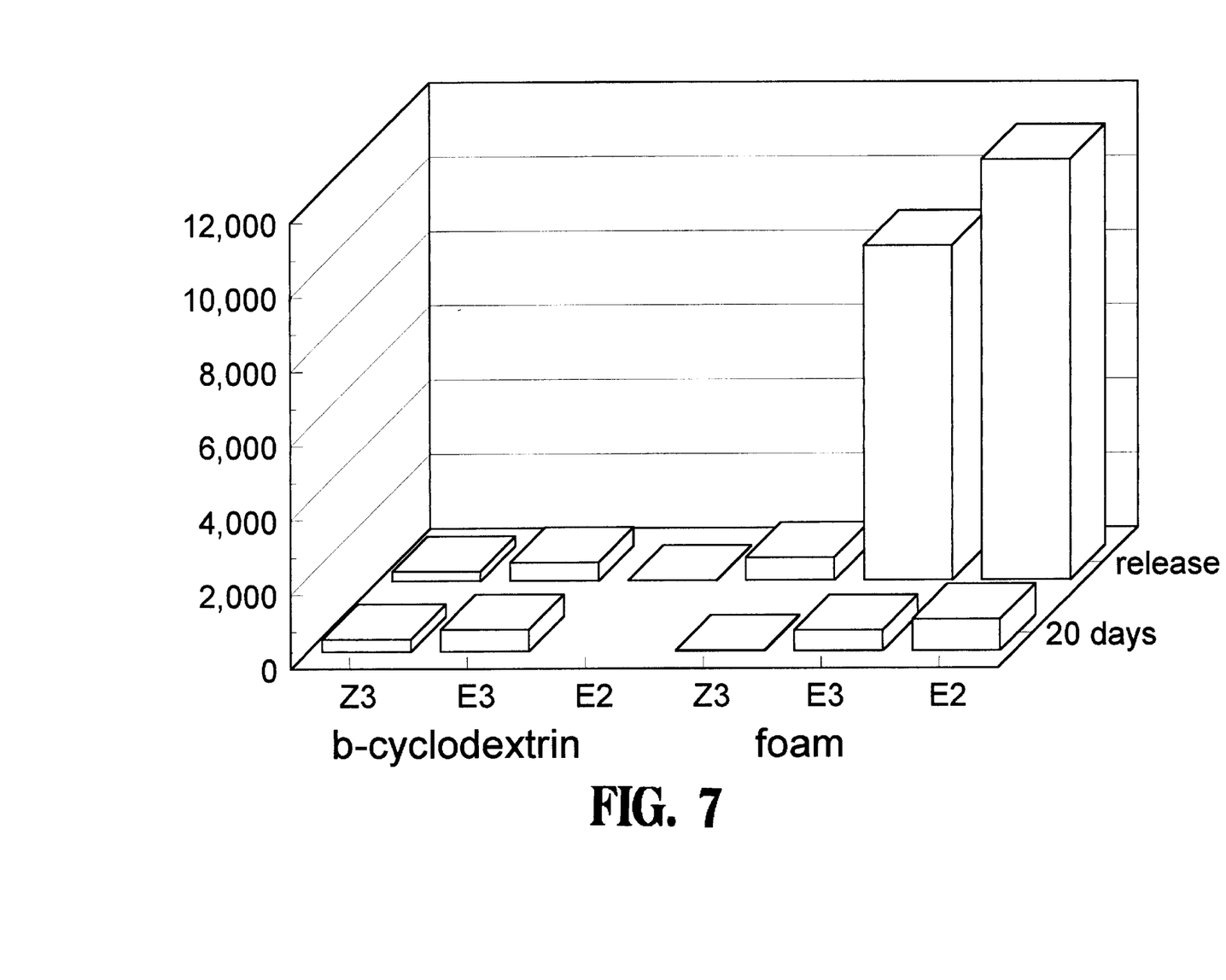
FIG. 7 shows only GC head space values for storage after 20 days in front row and release of odorant in rear row.
Figure 8:
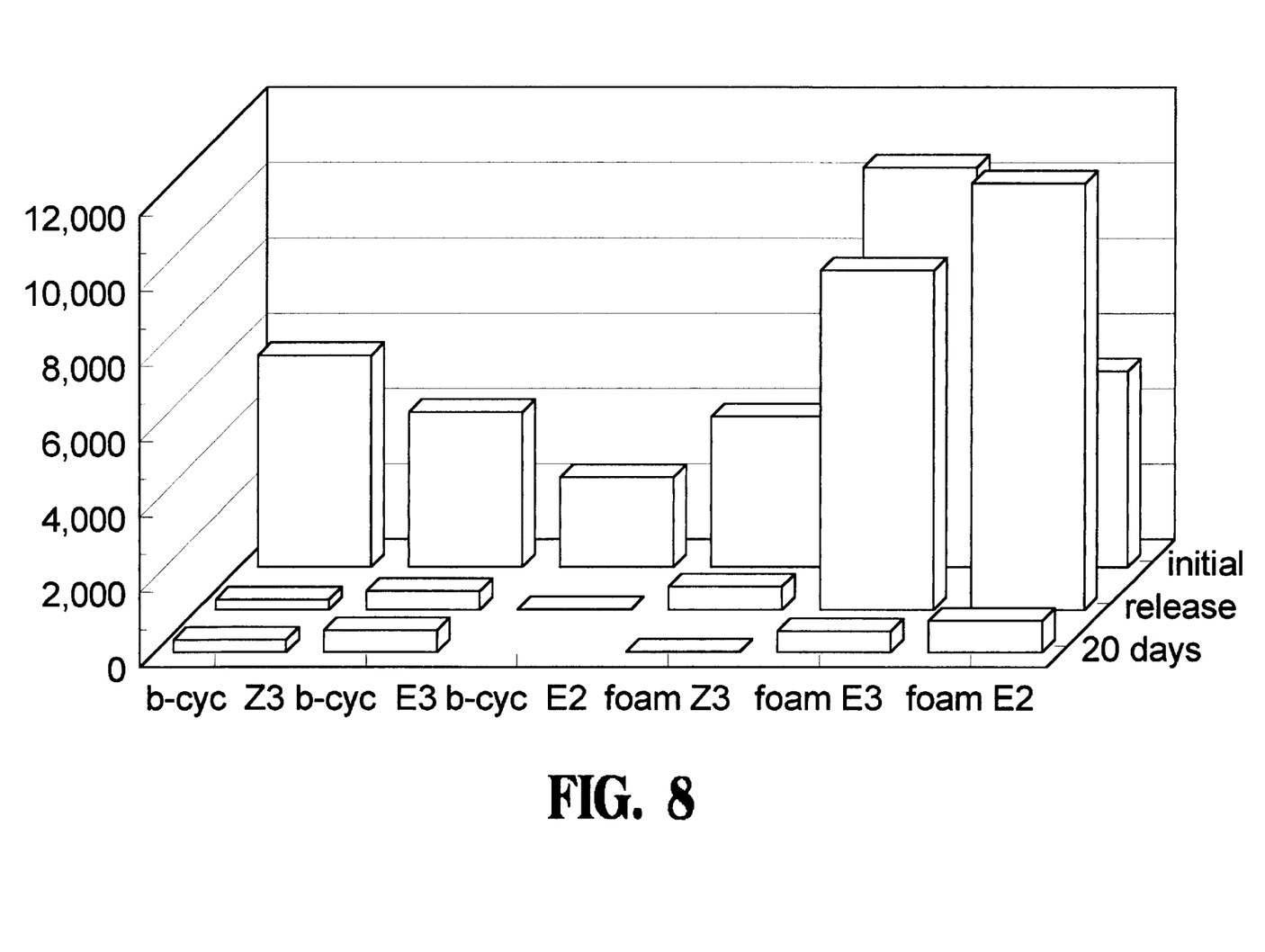
FIG. 8, from front to rear, shows GC head space analyses for odorants after 20 days storage, release, and initial values.

A more detailed comparison of β-cyclodextrin and starch-based microcellular foam are illustrated by FIGS. 7 and 8 and Table VIII. The graph values are arranged and presented in two figures for clarity. β-cyclodextrin was chosen to compare starch-based microcellular foam with because of its demonstrated ability to sequester odorant molecules in a guest/host relationship.

TABLE VIII

|  | β-cyclodext (Z)-3 | β-cyclodext (E)-3 | β-cyclodext (E)-2 | foam (Z)-3 | foam (E)-3 | foam (E)-2 |
| --- | --- | --- | --- | --- | --- | --- |
| initial | 5624 | 4121 | 2382 | 3994 | 10620 | 5213 |
| release | 261 | 500 | 10 | 618 | 9011 | 11328 |
| 20 days | 333 | 586 | 0 | 20 | 555 | 837 | values = uV/sec

The graph in FIG. 7 shows the values for all three isomers of (Z)-3-hexenal after storage for 20 days and release. Values for β-cyclodextrin samples are given by the left three bar sets and starch-foam by the right three sets. The twentieth day of storage shows comparable values for (E)-3 and (E)-2 hexenals on both media, while (Z)-3-hexenal is conserved to a greater degree on β-cyclodextrin, as noted previously in FIG. 5. A greater amount of all isomers was regenerated from starch-foam than β-cyclodextrin, probably due to the relative ease of destroying the starch-foam complex. Better results for β-cyclodextrin may have been obtained with more exhaustive extraction.

FIG. 8 summarizes values for initial, regeneration and storage after 20 days on β-cyclodextrin or starch-based microcellular foam. Note that a greater amount of (E)-2-hexenal was recovered than initially present, this is due to transformation of (Z)-3-hexenal, to the (E)-2 form, as noted earlier. It also shows that recovery of all forms of hexenal were quite comparable in β-cyclodextrin and starch-foam.

Figure 9:
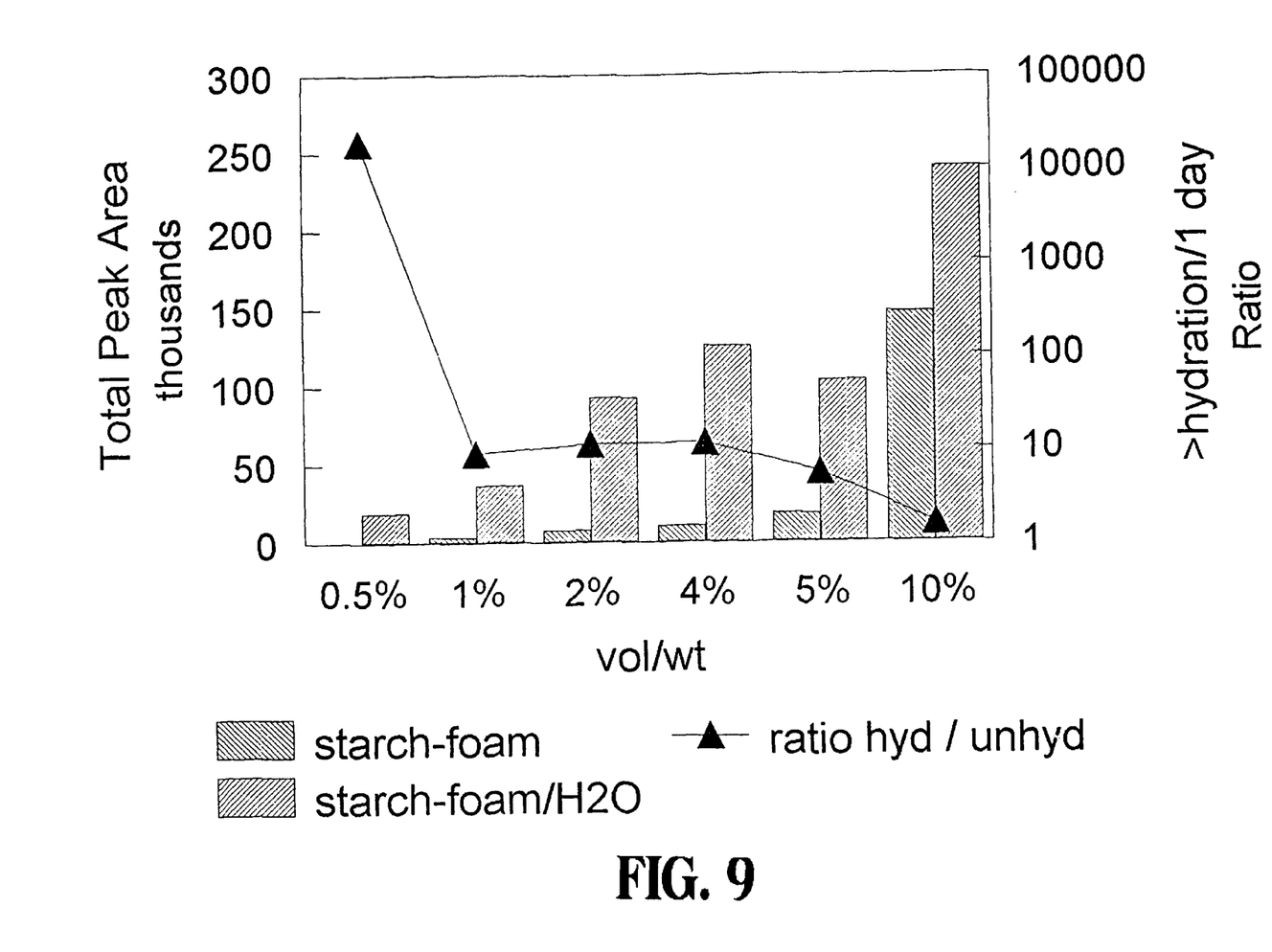
FIG. 9 compares (Z)-3-hexenal on starch-based microcellular foam, in concentrations varying from 0.5 to 10% wt/vol, for one day. Each pair of bars represents differing concentrations. Vapor samples were made after one day of storage, then recovery of (Z)-3-hexenal by hydration of complex. The triangles, connected by a line, represent ratio of recovered odorant to value prior to hydration.

Optimization. Optimization for the starch-foam hexenal (s) complex is shown in FIG. 9 and Table IX. Each pair of bars represents amounts of (Z)-3-hexenal in varying v/wt ratios on starch-based microcellular foam, after very limited storage time and after hydrating. The triangles in this figure represent the ratio (log scale on right) of regenerated (Z)-3-hexenal vapor to (Z)-3-hexenal vapor present before hydration. It becomes apparent that at ratios of less than 1% starch-foam is able to encapsulate (Z)-3-hexenal to the point where vapor pressure of the volatile is a trace. With subsequent hydration, the release of (Z)-3-hexenal is thousands of times greater than before hydration.

TABLE IX

| % vol/wt | Area 1 day | Area >hydration | Ratio >hyd/1 day |
| --- | --- | --- | --- |
| 0.5 | 1 | 19118 | 19118 |
| 1 | 4080 | 37091 | 9 |
| 2 | 8167 | 92740 | 11 |
| 4 | 10701 | 125982 | 12 |
| 5 | 18462 | 104021 | 6 |
| 10 | 147525 | 240241 | 2 |

The last figure suggests that (Z)-3-hexenal is sequestered at 0.5% vol/wt of starch-foam. This indicates the possibility that such complexes will completely protect the aldehyde from evaporation and/or decomposition.

Example 3

This example describes the preparation of a starch plastic by compression of the starch-based microcellular foams of the invention. Microcellular starch foams of wheat starch were made according to the procedures described in EXAMPLE 1 for slab samples. The slab foam samples were equilibrated for 48 hours at 50% relative humidity and 22° C. Samples that measured 7 inches in length, 2 inches in width and 0.5 inches in thickness were prepared. The samples were pressed between two polished, hardened steel plates at a force ranging from 1 to 120 MPa and preferably about 30 to 35MPa using a hydraulic press. The samples were simply pressed to reach the desired compressive force then promptly removed from the press. The samples were then trimmed with a small band saw into the shape of a tensile bar and tested according to ASTM D638M-91a. The flexural strength of the samples was measured on samples cut into bars of 1 cm in width and 12 cm in length. Flexural strength was measured according to ASTM D648-82.

The mechanical properties of the pressed starch foams were studied for samples that were made within 7 days or aged for 8 weeks at room temperature or in the cold (−15° C.). A comparative study was performed using polypropylene samples.

Results

The wheat starch foams were compressed under the pressures used into a dense, white, opaque material having the appearance of a plastic and will hereafter be referred to a starch plastic. The starch plastic had a smooth glossy appearance. Foams that were pressed at forces approaching 120 MPa became transparent. These observations were true for both corn and wheat starches although the results reported in Table X are for just starch plastics made from wheat starch foams.

The starch plastic control (made within the last 7 days) had nearly the same tensile strength and modulus of elasticity as the polypropylene sample. The flexural strength of the polypropylene was higher than that of the starch plastic. The aging treatments at room temperature or in the cold did not significantly affect the mechanical properties of the polypropylene. However, aging weakened the tensile and flexural strength of the starch plastic, especially in cold conditions. The modulus of elasticity was less affected by the aging process compared to the tensile and flexural strength parameters.

TABLE X

|  | Tensile Strength | | Flexural Strength | | Modulus | |
| --- | --- | --- | --- | --- | --- | --- |
|  | PolyPro | Starch | PolyPro | Starch | Polypro | Starch |
| Control | 25.7 | 22.2[a] | 34.5 | 25.0[a] | 1032[a] | 1052[b] |
| Aged Control | 27.1 | 16.0[b] | 30.3 | 23.6[a] | 969[a] | 1412[a] |
| Aged Cold Control | 26.1 | 6.7[c] | 30.1 | 7.51[d] | 1010[a] | 811[b] |

What is claimed is:

1. A starch-based microcellular foam comprising a solid phase matrix of gelatinized starch having an amylose content of at least 40% or greater amylose, said solid phase matrix having therein a network of small open cells having a liquid or solid substance encapsulated therein, wherein the density of said solid phase matrix in the absence of said encapsulated liquid or solid substance is about 0.32 gm/cm$^3$ or less, and the surface area is 50 m$^2$/gm or greater and wherein at least about 80% of said open cells of said matrix are about 10 μm or smaller in size.

2. The starch-based microcellular foam of claim 1, wherein said starch-based microcellular foam is prepared by:

(1) treating an aquagel prepared from gelatinized starch with a first exchange liquid, wherein said first exchange liquid comprises a nonaqueous liquid component which is effective for displacing water in the aquagel, said treatment comprising equilibrating said aquagel in said first exchange liquid for a time sufficient to displace at least about 80% of the water in said aquagel to thereby obtain an intermediate gel;

(2) displacing said first exchange liquid from said intermediate gel by equilibrating said gel with a second exchange liquid, wherein said second exchange liquid comprises a nonaqueous liquid component which is effective for displacing said first exchange liquid, said displacing comprising equilibrating for a time sufficient to displace at least about 80% of said first exchange liquid with said second exchange liquid, and (3) displacing said second exchange liquid with air.

3. The starch-based microcellular foam of claim 1, wherein said starch is selected from the group consisting of (a) unmodified starch, (b) starch that has been modified by hydrolysis or dextrinization, or has been modified to change the chemical structure of some of the D-glucopyranosyl units in the molecule by oxidation, esterification or etherification, (c) a mixture of unmodified starches, (d) a mixture of modified starches, and (e) a mixture of unmodified and modified starches.

4. A method of encapsulating a liquid or solid substance for later release, which comprises encapsulating said liquid or solid substance with a starch-based microcellular foam comprising a solid phase matrix of gelatinized starch having an amylose content of at least 40% or greater amylose, said solid phase matrix having therein a network of small open cells wherein the density of said solid phase matrix in the absence of said encapsulated liquid or solid substance is about 0.32 gm/cm$^3$ or less, and the surface area is 50 m$^2$/gm or greater and wherein at least about 80% of said open cells of said matrix are about 10 μm or smaller in size.

5. The method of claim 4 which further includes releasing said encapsulated liquid or solid substance by treating the foam with water.

* * * * *